United States Patent
Lee et al.

(10) Patent No.: US 8,799,197 B2
(45) Date of Patent: Aug. 5, 2014

(54) DATA PROCESSING METHOD AND APPARATUS FOR CLINICAL DECISION SUPPORT SYSTEM

(75) Inventors: Sung-Young Lee, Gyeonggi-do (KR); Asad Masood Khattak, Yongin-si (KR)

(73) Assignee: Industry Academic Cooperation Foundation of Kyung Hee University, Yongin-si (KR)

( * ) Notice: Subject to any disclaimer, the term of this patent is extended or adjusted under 35 U.S.C. 154(b) by 305 days.

(21) Appl. No.: 13/315,427

(22) Filed: Dec. 9, 2011

(65) Prior Publication Data

US 2013/0132312 A1    May 23, 2013

(30) Foreign Application Priority Data

Nov. 21, 2011   (KR) .................... 10-2011-0121846

(51) Int. Cl.
  *G06F 15/18*   (2006.01)
  *G06N 3/00*    (2006.01)
  *G06N 3/12*    (2006.01)

(52) U.S. Cl.
  USPC ........................................................ 706/13

(58) Field of Classification Search
  USPC ............................................................ 706/13
  See application file for complete search history.

(56) References Cited

U.S. PATENT DOCUMENTS 7,005,517 B2 *   2/2006   Lee et al. ...................... 540/122
2003/0058697 A1 *   3/2003   Tour et al. ..................... 365/200
2007/0094188 A1     4/2007   Pandya et al.
2010/0131438 A1 *   5/2010   Pandya et al. ................... 706/12

OTHER PUBLICATIONS

Kim, Ki-Hyeon et al. "A Clinical Decision Support System for Heart Disease Detection," School of Engineering, Information and Communications University, 2007 (5 pages, including English language abstract).
Yoo, Donghee, et al. "Semantic Web-based Clinical Decision Support System for Armed Forces Hospital," DOI: 10.3745/KIPSTB.2010.17B.4.317 (10 pages, including English language abstract).
Kim, Jeong Ah et al., "CDSS (Clinical Decision Support System) Architecture in Korea," International Conference on Convergence and Hybrid Information Technology 2008, pp. 700-703, IEEE Computer Society.

* cited by examiner

*Primary Examiner* — Michael B Holmes
(74) *Attorney, Agent, or Firm* — NSIP Law

(57) ABSTRACT

Provided is a data processing method for clinical decision support system. The data processing method provides an algorithm capable of performing parsing based on an Ontology technique and automatically updating rule database in order to reduce time and labor overloads accompanied by update of the rule database. According to an aspect, the data processing method includes inferring input data having a natural language format based on an Ontology technique to recognize at least one input rule included in the input data; inferring storage data having a natural language format and stored in rule database based on the Ontology technique to recognize at least one storage rule associated with the input rule from the storage data; comparing the input rule to the storage rule using a Self Evolutionary Rule-base algorithm; and updating the storage data stored in the rule database to the input data according to the result of the comparison.

7 Claims, 3 Drawing Sheets

DATA PROCESSING METHOD AND APPARATUS FOR CLINICAL DECISION SUPPORT SYSTEM

CROSS-REFERENCE TO RELATED APPLICATION

This application claims the benefit under 35 U.S.C. §119 (a) of a Korean Patent Application No. 10-2011-0121846, filed on Nov. 21, 2011, the entire disclosure of which is incorporated herein by reference for all purposes.

BACKGROUND

1. Field

The following description relates to a data processing method for clinical decision support system.

2. Description of the Related Art

For security and sharing of personal medical information, a recording system for storing and managing patients' medical records using electronic health recodes has been developed and utilized. The electronic health records contribute to provision of advanced medical services by sharing or exchanging medical information with various fields needing the medial information, as well as between medical institutes. Recently, with distribution of medical equipment capable of accurately measuring patients' health statuses and development of technologies including IT, NT and BT, private healthcare services such as Ubiquitous Healthcare have been introduced so that patients themselves can easily check their health statuses without having to visit hospitals.

In order to keep pace with the trend, studies into providing such healthcare services through a clinical decision support system are underway. The clinical decision support system is a computer-based support system designed to make a correct decision when a medical decision is needed, based on data measured or input from a patient and knowledge information of rule database. With realization of information of health and medical services, such as electronic health records and ubiquitous healthcare, concern with advanced medical services and reduction in time and cost is more increasing, and accordingly interest on the clinical decision support system is also increasing.

Electronic health records guidelines are generally stored in text files and are periodically updated by a user or system expert. In document "Clinical Decision Support System Architecture in Korea" by J. A. Kim, etc., International Conference on Convergence and Hybrid Information Technology, the authors have proposed inference mechanism with Electronic Health Record (HER) for existing hospital information systems. The inference mechanism can be applied to various healthcare fields including a clinical decision support system that is being actively studied.

Input data that is input to the clinical decision support system contains measurement is values about patients and knowledge about diseases. The input data is determined based on a rule, which generally is in the format of a natural language. The natural language is distinguished from constructed languages, such as machine languages, created for effective communications in specific technical fields. Since the natural language is different from machine languages used in computers or the like and computers can never understand the natural language, inputting data to a computer needs programming such as compiling for converting the natural language to a machine language. However, such programming needs help and intervention from experts, which is time consuming, resulting in low efficiency.

Furthermore, existing clinical decision support systems require very strict formats in applying an inference engine or in storing rules, so that a single rule storage does not allow the use of two or more inference engines having rules in different representational formats provided as input.

Therefore, in the case of a system dealing with expert content, like the clinical decision support system, data stored in rule database should be periodically updated with the help of medical doctors or programmers who are experts and participated in system manufacturing. However, the periodical update of data causes labor overheads as well as significant time consumption, resulting in inefficiency. These problems have become a major obstacle to application of the clinical decision support system to various fields.

Accordingly, in order to overcome the problems, a new clinical decision support system capable of efficiently updating rule database and allowing access of inference engines is needed.

SUMMARY

The following description relates to a data processing method for clinical decision support system, to which a Self Evolutionary Rule-base algorithm capable of automatically is updating rule database is applied in order to reduce time consumption and labor overloads accompanied by update of the rule database.

In one general aspect, a data processing method is provided for a clinical decision support system, including: inferring input data having a natural language format based on an Ontology technique to recognize at least one input rule included in the input data; inferring storage data having a natural language format and stored in rule database based on the Ontology technique to recognize at least one storage rule associated with the input rule from the storage data; comparing the input rule to the storage rule using a Self Evolutionary Rule-base algorithm; and updating the storage data stored in the rule database to the input data according to the result of the comparison.

Therefore, as described above, according to the data processing method for clinical decision support system, to which the Self Evolutionary Rule-base algorithm is applied, it is possible to quickly and efficiently update rule database by applying a generic storage structure to the rule database to support various storage formats and work with more than one inference engine, inferring a natural language having a variety of formats through a parser based on an ontology technique and then applying a comparison algorithm to the results of the inference.

Other features and aspects will be apparent from the following detailed description, the drawings, and the claims.

Figure 1:
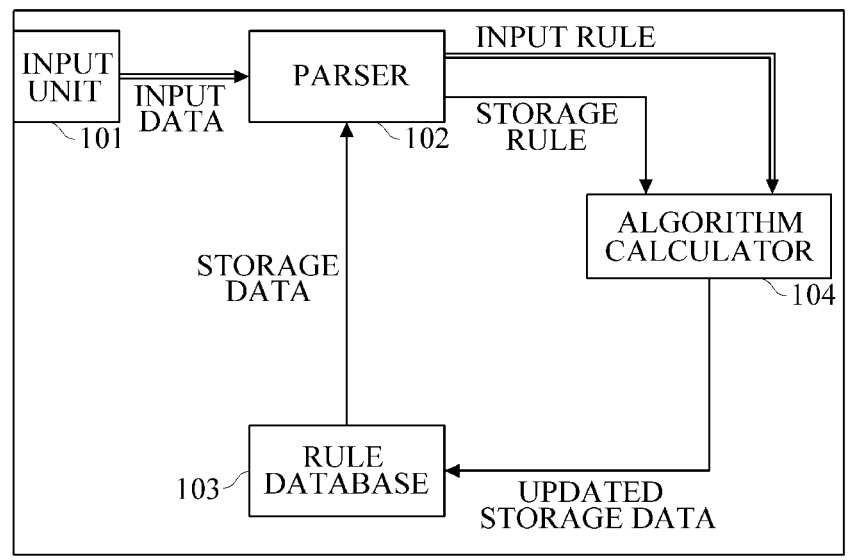
FIG. 1 is a diagram illustrating an example of a data processing apparatus of a clinical decision support system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

When data is stored in rule database or when storage rules are inferred from data stored in the rule database, generally, a strict data format is required, which is a characteristic of a general computer system and also the major cause of low efficiency. In order to overcome the problem, a method of combining an Ontology technique and a generic storage structure with a Self Evolutionary Rule-base algorithm has been proposed.

The following description relates to a method for efficiently processing data by applying the Ontology technique, the generic storage structure, and the Self Evolutionary Rule-base algorithm to a clinical decision support system.

Figure 2:
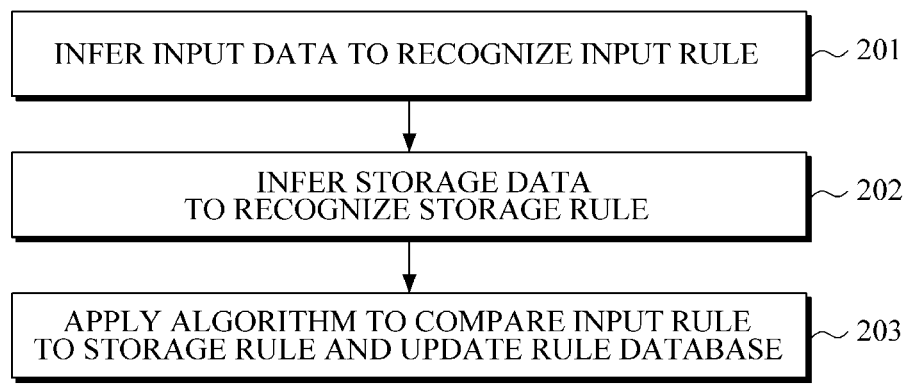
FIG. 2 is a flowchart illustrating an example of a data processing method for clinical is decision support system.

FIG. 1 is a diagram illustrating an example of a data processing apparatus of a clinical decision support system, to which a Self Evolutionary Rule-base algorithm (see FIG. 3) is applied, and FIG. 2 is a flowchart illustrating an example of a data processing method for clinical is decision support system.

Referring to FIGS. 1 and 2, the data processing method includes inferring input data having a natural language format based on the Ontology technique to recognize at least one input rule included in the input data (201); inferring storage data having a natural language format and stored in rule database 103 based on the Ontology technique to recognize at least one storage rule associated with the input rule from the storage data (202); and comparing the input rule to the storage rule by applying the Self Evolutionary Rule-base algorithm to the input rule and the storage rule, and updating the storage data to the input data according to the result of the comparison (203).

Each of the input rule and storage rule is composed of an item and a detail.

Referring to FIG. 1, the data processing apparatus of the clinical decision support system includes an input unit 101, the rule database 103, a parser 102, and an algorithm calculator 104. The input unit 101 receives input data having a natural language format. The rule database 103 stores storage data having a natural language format and is updated based on the input data. The parser 102 infers the input data and storage data having the natural language format to recognize at least one input rule included in the input data and at least one storage rule included in the storage data. The algorithm calculator 104 applies the Self Evolutionary Rule-base algorithm to compare the input rule to the storage rule, and updates the storage data stored in the rule database 103 according to the result of the comparison.

The input unit 101 receives input data containing health statuses and measurement values about patients, medical knowledge, medical inspections results, etc. The input data generally has a natural language format and is used as it is without translation to any machine language.

The rule database 103 stores the storage data in the natural language format. That is, a plurality of storage rules each consisting of an item and a detail are stored as the storage data in is the rule database 103. Content of the storage rules can be classified into data and facts. The data includes unchangeable values, for example, measurement values, health status values, disease-related values, etc. about patients. The facts are expert's knowledge about the situation/problem. That is, for example, in the medical field, the facts represent the symptoms of diseases, or medical treatments, etc. The output results of the clinical decision support system are based on the storage rules.

The parser 102 is a kind of data processing apparatus for recognizing input rules and storage rules from input data and storage data having the natural language format. The parser 102 applies the Ontology technique to recognize data in the natural language format. That is, the parser 102 uses the Ontology technique to infer the input data and the storage data, and recognizes at least one input rule and at least one storage rule based on the results of the inference.

The algorithm calculator 104 mainly functions to compare an item and detail of the input rule to those of the storage rule and update the rule database 103 based on the results of the comparison. The algorithm calculator 104 uses the Self Evolutionary Rule-base algorithm to update the rule database 103. That is, the Self Evolutionary Rule-base algorithm compares an item of the input rule to an item of the storage rule and adds, if the item of the input rule is a new item that is identical to no item of the storage rule, the input rule corresponding to the new item to the rule database 103. If the item of the input rule is identical to an item of the storage rule, the Self Evolutionary Rule-base algorithm compares the detail of the input rule to a detail of the storage rule, and corrects, if the detail of the input rule is different from the detail of the storage rule, the corresponding detail of the storage rule to thereby update the rule database 103.

Successively referring to FIG. 2, in operation 201 of inferring the input data to recognize the input rule, the input data contains measurement values about patients, medical knowledge, etc. The input data is generally in the natural language format. In order to use the input data in a computer, a process of compiling the input data to a machine language understandable by the computer or of adding an interface is needed, however, such a process may result in efficiency deterioration. For this reason, the parser 102 uses the Ontology technique to make the computer understand the natural language as it is.

That is, parsing based on the Ontology technique is needed since the computer considers natural languages only as a collection of characters. The Ontology technique builds a conceptual model about an arbitrary object which human beings can see, hear or feel in the world, in a format that can be handled by a computer, thereby making the computer understand natural languages as its own language.

By using the parser 102 based on the Ontology technique to infer input data in the natural language format, at least one input rule included in the input data can be recognized.

Operation 202 of inferring the storage data to recognize at least one storage rule is to recognize at least one storage rule from storage data stored in the rule database 103. Storage rules stored in the rule database 103 are in the natural language format, like input rules. Accordingly, the parser 102 to which the same Ontology technique as that applied to recognize the input rule is applied is used to infer the storage data and recognize the storage rule.

The storage data is stored in the rule database 103 using a generic storage structure. The generic storage structure, which uses a concept of generic programming, can freely store data without being subject to limitation about file formats. Accordingly, the storage data in the natural language format also can be stored as it is without compiling to a machine language.

In summary, by using the Ontology technique and generic storage structure, it is possible to process data in the natural language format without any format conversion. That is, this makes it possible to simultaneously apply different inference engines having input is representational formats when accessing the rule database 103 to recognize rules and infer content, resulting in more effective inference. Also, the Self Evolutionary Rule-base algorithm is run on a generic storage structure.

In operation 203 of updating the rule database 103, the Self Evolutionary Rule-base algorithm is applied to compare the input rule to the storage rule and update the rule database 103 according to the results of the comparison.

Figure 3:
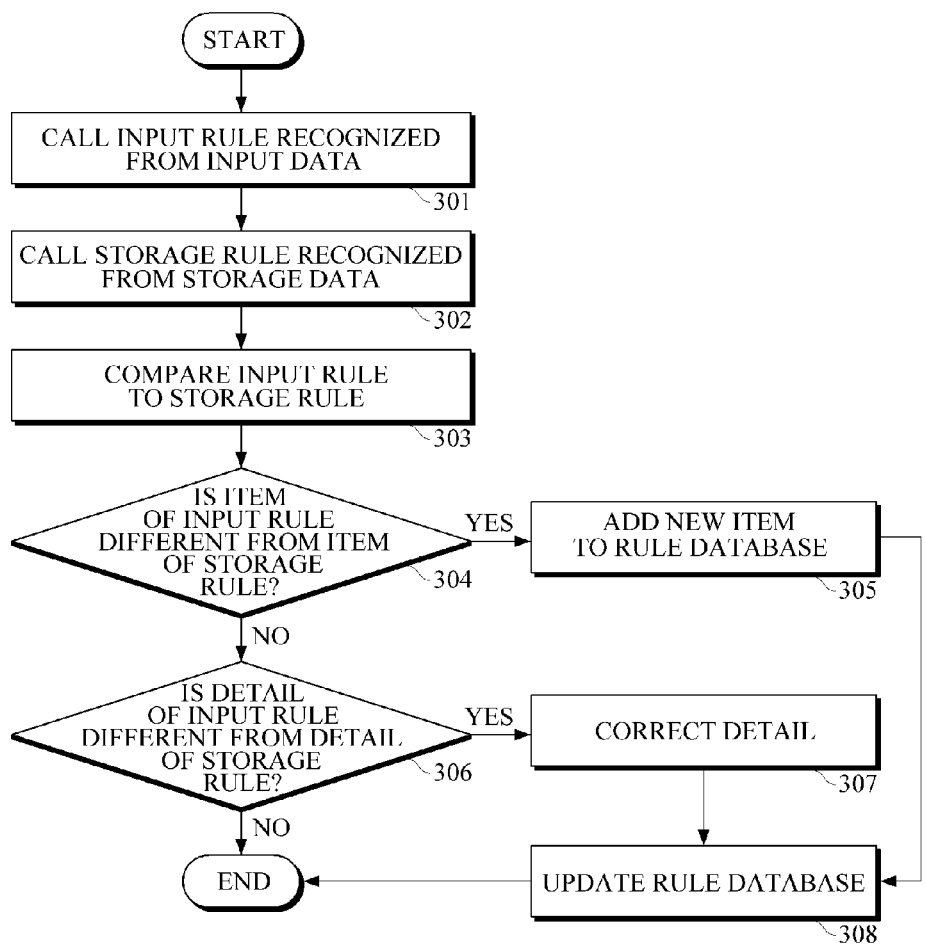
FIG. 3 is a flowchart illustrating a Self Evolutionary Rule-base algorithm.

FIG. 3 is a flowchart illustrating the Self Evolutionary Rule-base algorithm.

Referring to FIGS. 1 and 3, the algorithm calculator 104 calls at least one input rule recognized from input data (301), and at least one storage rule recognized from storage data in correspondence to the input rule (302).

Then, the algorithm calculator 104 compares the input rule to the storage rule acquired from the rule database (103) (303).

First, the algorithm calculator 104 compares at least one item included in the input rule to at least one item included in the storage rule (304). If an item included in the input rule is identical to no item included in the storage rule, the algorithm calculator 104 considers the input rule corresponding to the item as a new input rule, and adds the new input rule to the rule database 103 (305).

On the contrary, if the item included in the input rule is identical to the item included in the storage rule, the algorithm calculator 104 compares a detail included in the input rule to a detail included in the storage rule having the same item as that of the input rule (306). If the detail of the input rule is identical to the detail of the storage rule, the algorithm calculator 104 terminates the algorithm.

If the detail included in the input rule is different from the corresponding detail included in the storage rule, that is, if a new detail is found, the algorithm calculator 104 substitutes the corresponding detail included in the storage rule by the new detail (307).

As described above, the Self Evolutionary Rule-base algorithm performs comparison and additional storage, thereby finally updating the rule database 103.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A data processing method for a clinical decision support system, the method comprising:
    inferring input data having a natural language format based on an Ontology technique to recognize an input rule coming from the input data;
    inferring storage data having a natural language format and stored in rule database based on the Ontology technique to recognize a storage rule associated with the input rule from the storage data;
    comparing the input rule to the storage rule using a Self Evolutionary Rule-base algorithm; and
    updating the storage data stored in the rule database to the input data according to the result of the comparison,
    wherein each of the input rule and the storage rule is composed of an item and a detail, and in response to a result of comparing indicating that at least one item included in the input rule is a new item that is not identical to an item included in the storage rule, the updating of the storage data comprises adding the input rule including the new item to the rule database.

2. The data processing method of claim 1, wherein in response to the result of the comparing indicates that at least one item included in the input rule is identical to an item included in the storage rule and a detail of the item of the input rule is different from a detail of the item of the storage rule, the updating of the storage data comprises substituting the detail of the item of the storage rule by the detail of the item of the input rule.

3. The data processing method of claim 1, wherein the storage data is stored in the rule database using a generic storage structure.

4. A data processing apparatus comprising:
    an input unit configured to receive input data having a natural language format;
    a rule database configured to store storage data having the natural language format, wherein the storage data is updated based on the input data;
    a parser configured to infer the input data and the storage data having the natural language format to recognize an input rule included in the input data a storage rule included in the storage data;
    an algorithm calculator configured to apply a Self Evolutionary Rule-base algorithm to compare the input rule to the storage rule, and to update the storage data stored in the rule database according to the result of the comparison,
    wherein each of the input rule and the storage rule is composed of an item and a detail, and in response to a result of comparing indicating that at least one item included in the input rule is a new item that is not identical to an item included in the storage rule, the updating of the storage data comprises adding the input rule including the new item to the rule database.

5. The data processing apparatus of claim 4, wherein the rule database stores the storage data in the natural language format using a generic storage structure.

6. The data processing apparatus of claim 4, wherein the parser uses an Ontology technique to infer the input data having the natural language format and the storage data stored in the rule database, thereby recognizing the input rule and the storage rule.

7. The data processing apparatus of claim 4, wherein, in response to the result of the comparison indicates that at least one item included in the input rule is identical to an item included in the storage rule and a detail of the item of the input rule is different from a detail of the item of the storage rule, the algorithm calculator substitutes the detail of the item of the storage rule by the detail of the item of the input rule.

* * * * *